(12) United States Patent
Harms

(10) Patent No.: US 6,670,476 B2
(45) Date of Patent: Dec. 30, 2003

(54) RESOLUTION OF TRANS-7-(HYDROXY-METHYL)OCTA-HYDRO-2H-PYRIDO[1,2-A]PYRAZINE

(75) Inventor: Arthur E. Harms, Niskayuna, NY (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/066,907

(22) Filed: Nov. 13, 2001

(65) Prior Publication Data

US 2003/0096821 A1 May 22, 2003

Related U.S. Application Data

(60) Provisional application No. 60/250,074, filed on Nov. 29, 2000.

(51) Int. Cl.[7] ............................................ C07D 471/04
(52) U.S. Cl. ....................................................... 544/349
(58) Field of Search ................................. 544/350, 349

(56) References Cited

U.S. PATENT DOCUMENTS 5,122,525 A 6/1992 Bright et al.
5,185,449 A 2/1993 Godek et al.
5,852,031 A 12/1998 Desai et al.
6,231,833 B1 * 5/2001 Desai et al. .................. 424/9.1

FOREIGN PATENT DOCUMENTS

EP         0569387         12/1991

* cited by examiner

*Primary Examiner*—John M. Ford
*Assistant Examiner*—Thomas McKenzie
*(74) Attorney, Agent, or Firm*—P. C. Richardson; P. H. Ginsburg; I. Nissenbaum

(57) ABSTRACT

The invention provides a process for the optical resolution of a racemic mixture, or an optically enriched mixture, of trans-7-(hydroxymethyl)octa-hydro-2H-pyrido-1,2a)pyrazine, a key intermediate for preparing pharmacologically active 2,7-substituted octahydro-1H-pyrido[1,2-a]pyrazine derivatives useful in the treatment of disorders of the dopamine system. The process of the invention involves use of D-(−) or L-(+)naproxen as a resolving agent.

12 Claims, 1 Drawing Sheet

RESOLUTION OF TRANS-7-(HYDROXYMETHYL)OCTA-HYDRO-2H-PYRIDO[1,2-A]PYRAZINE

This application claims the benefit of provisional application Ser. No. 60/250,074, filed Nov. 29, 2000.

BACKGROUND OF THE INVENTION

The present invention relates to a process for the optical resolution of a key intermediate for preparing pharmacologically active 2,7-substituted octahydro-1H-pyrido[1,2-a]pyrazine derivatives, such as (7S,trans)-2-(2-pyrimidinyl)-7-(hydroxymethyl)octahydro-2H-pyrido(1,2-a)pyrazine, which are disclosed in U.S. Pat. No. 5,852,031, the contents of which are hereby incorporated by reference. These pyrazine compounds are ligands with specificity for dopamine receptor subtypes, especially the dopamine D4 receptor, within the animal body, and are therefore useful in the treatment of disorders of the dopamine system. The process of the present invention involves resolution of trans-7-(hydroxymethyl)octahydro-2H-pyrido(1,2-a)pyrazine using D-(−) or L-(+)naproxen.

Previously, the desirable optically resolved pyrazine compounds were obtained by later-stage resolution using D-(−) or L-(+)-tartaric acid, as disclosed in European Patent No. 569387. The present method has the advantage of minimizing material losses incurred by conducting resolutions after a multistep synthetic sequence, and results in a more efficient, higher-yielding process for preparing the (7S,trans)-2-(2-pyrimidinyl)-7-(hydroxymethyl)octahydro-2H-pyrido(1,2-a)pyrazines.

SUMMARY OF THE INVENTION

The present invention relates to a process for separating a racemic mixture, or an optically enriched mixture, of trans-7-(hydroxymethyl) octahydro-2H-pyrido(1,2-a)pyrazine containing a first enantiomer having the formula:

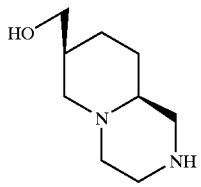

and a second enantiomer having the formula:

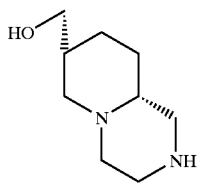

the process comprising:
reacting the racemic mixture, or the optically enriched mixture, with (+)-naproxen or (−)-naproxen to form, respectively, a diastereomeric mixture of the (+)- or (−)-naproxen salts of each of the enantiomers; separating each of the diastereomeric (+)- or (−)-naproxen salts; and if desired, converting the respective naproxen salt of each enantiomer to the free base thereof.

The present invention further provides a salt of a compound with a substance selected from the group consisting of (+)-naproxen and (−)-naproxen, said compound having the formula

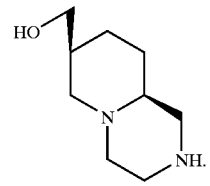

The present invention also provides a salt of a compound compound with a substance selected from the group consisting of (+)-naproxen and (−)-naproxen, said compound having the formula

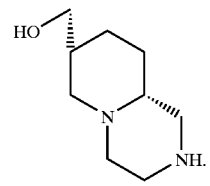

DETAILED DESCRIPTION OF THE INVENTION

Figure 1:
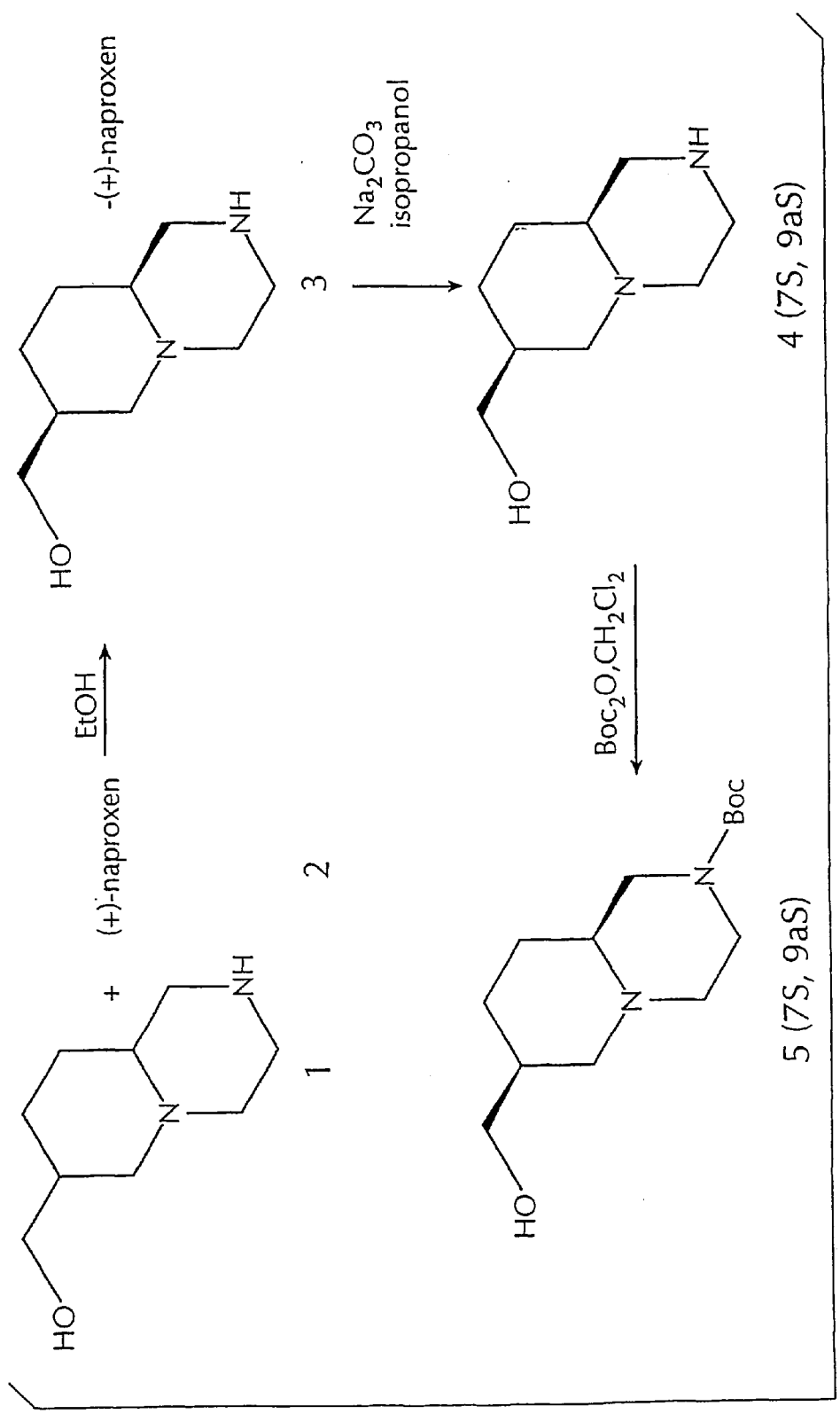
FIG. 1 shows a synthetic pathway for preparing key intermediates in the manufacture of biologically active 2,7-substituted octahydro-1H-pyrido[1,2-a]pyrazine derivatives.

As illustrated in the accompanying FIGURE, the present invention provides a process for resolution of a racemic mixture, or an optically enriched mixture, of pyrazines which comprises forming a (+)- or (−)-naproxen salt (2) of the pyrazines (1) and thereafter, in a separating step, converting the respective (+)- or (−)-naproxen salt to the free-base of the associated enantiomer (3). Preferably, in one implementation of the process of the invention, the racemic mixture, or the optically enriched mixture, is reacted with (+)-naproxen. The amount of (+)-naproxen added in the reaction is from about 0.5 equivalent to about 1.0 equivalent, and is preferably about 0.5 equivalent. In the process, the separating step comprises isolating an insoluble (+)-naproxen salt from a soluble (+)-naproxen salt, and the insoluble (+)-naproxen salt is a salt of the first enantiomer.

Alternatively, the process of the present invention may be performed wherein the racemic mixture, or the optically enriched mixture, of pyrazines is reacted with (−)-naproxen. In such case, the separating step comprises isolating an insoluble (−)-naproxen salt from a soluble (−)-naproxen salt, and the insoluble (−)-naproxen salt is a salt of the second enantiomer. In one embodiment, the process comprises a reacting step which comprises contacting the racemic mixture, or the optically enriched mixture, with (+)-naproxen to form a precipitate in a solution, wherein the precipitate is the (+)-naproxen salt of the first enantiomer; and the process further comprises separating the precipitate from the solution; and further comprising converting the (+)-naproxen salt of the first enantiomer to the free-base thereof.

The reacting step optionally comprises contacting the racemic mixture, or the optically enriched mixture, with (−)-naproxen to form a precipitate in a solution, the solution comprising the (−)-naproxen salt of the first enantiomer dissolved therein; the separating step comprises separating the precipitate from the solution and evaporating the solution so as to provide the salt of the first enantiomer; and further comprising converting the (−)-naproxen salt of the first enantiomer to the free-base thereof.

Accordingly, in the process of the present invention, trans-7-(hydroxymethyl)octahydro-2H-pyrido(1,2-a) pyrazine is resolved using (+)-naproxen or (−)-naproxen. The pyrazine is reacted with either (+)-naproxen or (−)-naproxen in an inert polar solvent. Suitable solvents include methanol, ethanol, isopropanol, ethyl acetate, diethyl ether and tetrahydrofuran, or mixtures thereof. Ethanol is a preferred solvent. The temperature of the reaction is not critical. Generally, the reaction mixture will be heated to a temperature sufficient to dissolve the starting material (i.e., about 30 to about 50° C., preferably about 40° C.) and then allowed to cool. Upon cooling, one of the diastereoisomeric (+)-naproxen or (−)-naproxen salts precipitates. When the (+)-naproxen salt is formed, the 7R enantiomer remains in solution and the 7S enantiomer precipitates. When the (−)-naproxen salt is formed, the 7S enantiomer remains in solution and the 7R enantiomer precipitates. If the desired enantiomer remains in solution, it is recovered by evaporating the liquid.

In order to convert the resulting isolated salt to the free base, any suitable method known in the art may be applied. Preferably, the salt is dissolved in water and the pH is raised to between about 10 to about 14, preferably about pH 12, using a base, such as sodium hydroxide, sodium bicarbonate, sodium carbonate, potassium hydroxide, potassium bicarbonate, potassium carbonate, ammonium hydroxide, and the like. The free base pyrazine is extracted from the aqueous layer using an inert non-polar solvent, such as isopropyl ether, diethyl ether, 1,1,1-trichloroethane, or methylene chloride, preferably the latter.

Pharmacologically useful pyrazine compounds may be prepared using the optically resolved intermediates as described herein. Among the uses are the amelioration of the symptoms of anxiety and other psychiatric conditions in a human subject. Methods for further synthetic elaboration of the optically resolved pyrazines to the pharmaceutical targets are disclosed in U.S. Pat. No. 5,852,031. The pyrazines prepared thereby are administered in accordance with methods known in the art in an effective amount of about 2 to about 200 mg/day, in single or divided daily doses. In particular cases, dosages outside that range are prescribed at the discretion of the attending physician. The preferred route of administration is generally oral, but parenteral administration (e.g., intramuscular, intravenous, intradermal) will be preferred in special cases, e.g. where oral absorption is impaired as by disease, or the patient is unable to swallow. These compounds are generally administered in the form of pharmaceutical compositions comprising a pharmaceutically acceptable vehicle or diluent. Such are generally formulated in a conventional manner utilizing solid or liquid vehicles or diluents as appropriate to the mode of desired administration: for oral administration, in the form of tablets, hard or soft gelatin capsules, suspensions, granules, powders and the like; and, for parenteral administration, in the form of injectable solutions or suspensions, and the like.

The present invention is illustrated, but not limited, by the following examples.

EXAMPLE 1

Diastereomeric Salt 2 of trans-7-(hydroxymeth-yl) octahydro-2H-pyr-ido(1,2-a)pyrazine Five grams g (29.2 mmol) of racemic trans-7-(hydroxymethyl)octa-hydro-2H-pyrido(1,2-a)pyrazine (rac-1) were dissolved in 25 ml of ethanol. (+)-Naproxen (3.2 g, 13.9 mmol) was added. Upon stirring, a solid began to precipitate. After stirring at room temperature for 48 hours the reaction was filtered and the solids dried. The diastereomeric salt (2; 3.1 grams) of trans-7-(hydroxymethyl) octahydro-2H-pyrido(1,2-a)pyrazine was thereby obtained (56% yield based on one enantiomer). $[\alpha]_D=-13.4$ (c=1.11, MeOH).

EXAMPLE 2

(7S,trans)-7-(Hydroxymethyl)octahydro-2H-pyrido(1,2-a)pyrazine (7S-3)

A solution of 3.0 g of diastereomeric salt (2) of trans-7-(hydroxymeth-yl)octahydro-2H-pyrido(1,2-a)pyrazine (7.49 mmol) in isopropanol was heated to reflux. 4.0 g of $Na_2CO_3$ (37.4 mmol) was added and the mixture was refluxed for 17 hr. The reaction was cooled to room temperature and filtered. The solids were washed with isopropanol and the filtrate was concentrated to dryness. The solids thus obtained were treated with hot toluene and filtered to remove insoluble salts. The filtrate was cooled and filtered to yield 0.9 g of a white solid (7S-3; 70%). $[\alpha]_D=-24.8°$ (c=0.895, MeOH). An authentic sample of (7S,trans)-7-(hydroxymethyl)octahydro-2H-pyrido(1,2-a)pyrazine showed $[\alpha]_D=-27.0°$ (c=0.895, MeOH) indicating that the material produced here was approximately 92% ee.

What is claimed is:

1. A process for separating a racemic mixture, or an optically enriched mixture, of a first enantiomer of the formula

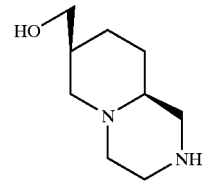

and a second enantiomer of the formula

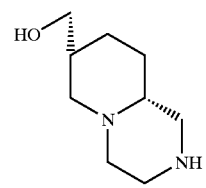

comprising:
reacting the racemic mixture, or the optically enriched mixture, with (+)-naproxen or (−)-naproxen to form respectively a diastereomeric mixture of the (+)- or (−) naproxen salts of each of the enantiomers; and separating each of the diastereomeric (+)- or (−)-naproxen salts.

2. The process of claim 1, further comprising, after said separating step, converting at least one of the (+)- or (−)-naproxen salts to the free-base of the respective separated enantiomers.

3. The process of claim 1, wherein said racemic mixture, or the optically enriched mixture, is reacted with (+)-naproxen.

4. The process of claim 3, wherein said separating step comprises isolating an insoluble (+)-naproxen salt from a soluble (+)-naproxen salt.

5. The process of claim 4, wherein said insoluble (+)-naproxen salt is a salt of the first enantiomer.

6. The process of claim 1, wherein the racemic mixture, or the optically enriched mixture, is reacted with (−)-naproxen.

7. The process of claim 6, wherein said separating step comprises isolating an insoluble (−)-naproxen salt from a soluble (−)-naproxen salt.

8. The process of claim 7, wherein said insoluble (−)-naproxen salt is a salt of the second enantiomer.

9. The process of claim 1, wherein said reacting step comprises contacting the racemic mixture, or the optically enriched mixture, with (+)-naproxen to form a precipitate in a solution, said precipitate being the (+)-naproxen salt of the first enantiomer; said separating step comprises separating the precipitate from the solution; and further comprising converting the (+)-naproxen salt of the first enantiomer to the free-base thereof.

10. The process of claim 1, wherein said reacting step comprises contacting the racemic mixture with (−)-naproxen to form a precipitate in a solution, the solution comprising the (−)-naproxen salt of the first enantiomer dissolved therein; said separating step comprises separating the precipitate from the solution and evaporating the solution so as to provide the salt of the first enantiomer; and further comprising converting the (−)-naproxen salt of the first enantiomer to the free-base thereof.

11. A salt of a compound with a substance selected from the group consisting of (+)-naproxen and (−)-naproxen, said compound having the formula

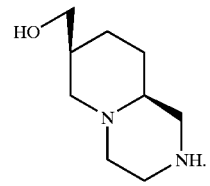

12. A salt of a compound with a substance selected from the group consisting of (+)-naproxen and (−)-naproxen, said compound having the formula

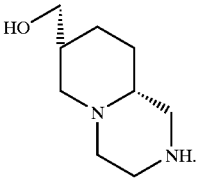

* * * * *